US006602233B1

(12) United States Patent
Palumbo et al.

(10) Patent No.: US 6,602,233 B1
(45) Date of Patent: Aug. 5, 2003

(54) EASY TO PLACE AND DETACH ADHESIVE FAECAL MANAGEMENT COLLECTOR

(75) Inventors: Gianfranco Palumbo, Bad Homburg (DE); Vincenzo D'Acchioli, Kelkheim am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/445,930

(22) PCT Filed: Jun. 26, 1998

(86) PCT No.: PCT/US98/13363

§ 371 (c)(1), (2), (4) Date: Dec. 20, 1999

(87) PCT Pub. No.: WO99/00088

PCT Pub. Date: Sep. 7, 1999

(30) Foreign Application Priority Data

Jun. 28, 1997 (EP) .......... 97110602
Jun. 28, 1997 (EP) .......... 97110603
Jun. 28, 1997 (EP) .......... 97110604

(51) Int. Cl.[7] .......... A61F 5/44

(52) U.S. Cl. .......... 604/355; 604/385.19

(58) Field of Search .......... 604/327, 331, 604/337, 338, 339, 341, 342, 348, 355, 385.19, 332–336, 340, 343, 344, 345

(56) References Cited

U.S. PATENT DOCUMENTS 3,522,807 A * 8/1970 Millenbach .......... 128/283
3,734,096 A * 5/1973 Millenbach .......... 128/383
4,784,656 A * 11/1988 Christian .......... 604/355
5,593,397 A * 1/1997 La Gro .......... 604/355
6,350,256 B1 * 2/2002 Palumbo et al. .......... 604/339
6,395,955 B1 * 5/2002 Roe et al. .......... 604/361
6,398,768 B1 * 6/2002 Palumbo et al. .......... 604/355
6,406,464 B1 * 6/2002 Palumbo et al. .......... 604/355
2002/0128614 A1 * 9/2002 Cinelli et al. .......... 604/332

FOREIGN PATENT DOCUMENTS

EP 0 753 290 A 1/1997
GB 1 078 588 A 8/1967
GB 1 092 274 A 11/1967
GB 2 116 849 A 10/1983
GB 2 140 692 A * 12/1984 .......... A61F/5/44

* cited by examiner

*Primary Examiner*—Weilun Lo
*Assistant Examiner*—Michael G. Bogart
(74) *Attorney, Agent, or Firm*—Leonard W. Lewis; Erich D. Hemm

(57) ABSTRACT

The present invention relates to faecal management devices for babies, children or adults, to be adhesively attached in a releasable manner to the perianal area of the wearer, said devices being particularly easy to put in place and particularly easy to detach after use. Claimed and described is a fecal management device (10) comprising a bag (11), said bag (11) having an aperture (21) and a flange (12) surrounding said aperture (21) said flange (12) having a wearer facing portion (23) and a garment facing portion (22), wherein said wearer facing portion (23) comprises a layer of adhesive (20) for releasable attachment to the perianal area of a wearer, characterized in that said flange (12) is provided with at least two non-adhesive lobes, i.e. one or more placement lobes (13) or one or more detachment lobes (14) or a combination thereof.

7 Claims, 4 Drawing Sheets

10
18
11
T
L
22
23
13
29
15
16
20
17
21
28
12
14
19
30
T
L

EASY TO PLACE AND DETACH ADHESIVE FAECAL MANAGEMENT COLLECTOR

FIELD OF THE INVENTION

The present invention relates to faecal management devices for babies, children or adults, to be adhesively attached in a releasable manner to the perianal area of the wearer, said devices being particularly easy to put in place and particularly easy to detach after use.

BACKGROUND

Faecal management devices are known articles of manufacture that are designed to be worn principally by incontinence sufferers and in particular by bedridden patients. Such faecal management devices are attached to the perianal area of the wearer and are intended to entrap and immediately contain faecal material and other bodily discharges.

Such devices as they are mostly known today are constituted of a relatively long and narrow tube, at one extremity of which is positioned the aperture and the attachment device, which can be adhesive. Such bags are disclosed in, e.g. U.S. Pat. No. 3,577,989.

A problem naturally associated with these devices is their attachment to the human body. The approach which is mostly used in the field is to provide the device with an adhesive flange, which will stick to the perianal area. U.S. Pat. Nos. 3,522,807 and 3,734,096 disclose faecal receptacles having an adhesive flange surrounding the aperture in the device, for attachment to the body of the patient in nursing or medical applications; said flange contains a plurality of tabs extending outwardly from the aperture and said tabs are covered with adhesive in the same manner as the rest of the flange and thus are designed to serve as adhering aids, and must be covered by a release means before use of the receptacles.

U.S. Pat. No. 5,593,397 addresses the problem of how to more conveniently remove the release paper which typically covers the adhesive parts of the faecal management device. Disclosed is a single tab on the flange and a corresponding single tab on the release paper, provided to help in peeling the release paper off the flange. The lobe of the flange is also thought to be of help when detaching the device. The provision of only one lobe may be unsatisfactory both for the detachment of the release paper and for the removal of the device considering the typical conditions under which such a device is handled. A caretaker may, for example, when dealing with a bedridden patient, have only one hand available for the application of the device, or for detachment find the patient lying in an undesirable position, in which the single lobe may not be accessible.

In GB-A-2, 116,849, it was attempted to provide an adhesive faecal incontinence device which, among other properties, was easier to put in place on the patient. The solution brought up by GB-A-2, 116,849 is, however, quite complex, involving individually removable sections of the release layer covering the adhesive layer on the flange surrounding the aperture, said sections having to be removed in a predetermined sequence in order to ensure optimum adherence.

Besides and in connection with optimum adherence, the proper placement of the device is a key issue in the field of faecal management devices. Total or substantial misplacement of the device will lead to a severe misfunctioning, in particular incomplete collection of faeces and leaking. If the aperture of the faecal management device is not sufficiently in registry with the anal opening, substantial pressure, in particular on the flanges of the device, can build up in the defecation process. Such substantial pressure can lead to the detachment of the adhesively secured device, obviously entailing the most unwanted consequences.

If the misplacement of the device is recognized before use, the placement of the device is normally corrected, typically by the carer. The necessary detachment and reattachment of the device means an additional stress on the affected areas of skin of the wearer. Many wearers, who make use of faecal management devices have a sensitive skin due to their age, whether very old or very young, and furthermore sometimes also suffer from skin irritations. Proper placement of the device in the first place is therefore highly desirable.

The faecal management devices which are disclosed in the mentioned prior art are normally handled and placed onto the skin of the wearer by using the flange itself. One of the first necessary handling steps is to remove the release paper from the adhesive surface of the flange. When then placing the device, the caretaker will normally touch the adhesive area of the flange with the fingers and leave finger marks. Such marks will reduce the adhesive force of the affected areas, if dirt is deposited from the fingers or if an adhesive is used, which tends to adhere less on a second contact with a surface.

Furthermore, during application of the faecal management device to the wearer by holding the flange, pressure typically needs to be exercised upon the flange. However, as a result the flange may suffer deformation, such deformation leading to a poorer performance of the device, in particular to a poorer adhesion, discomfort or possibly leaking of the device.

In Kokai Patent Application No. HEI8 (1996) 117 261, an external accessory is described to help put the adhesive part of the disclosed diaper in place. Such a tool may be a help in the placement of such an incontinence product when compared to the placement without any aide. However, the successful use of such tool will require some training, in particular if the tool, as it seems to be the case here, is not specifically designed for its purpose.

Yet another problem associated with faecal management devices is their handling after detachment. Since they regularly are a source of malador and possibly of leakage, the caretaker will typically try and seal the bag for disposal, e.g. by sticking opposite parts of the adhesive flange together. In doing so the caretaker might face the problem of unwanted sticking of the fingers onto the adhesive flange or between two parts of the adhesive flange. Also, the caretaker might not want to touch the adhesive parts of the flange, since they get easily soiled due to their adhesive nature.

In attempting to overcome all the aforementioned problems relating to the prior art, it has now been found that adhesive faecal management devices can be designed which have excellent ease of placement properties, through the use of a simple, but efficient device. The same design does not only greatly help in placing the device but also assists in detachment and handling after detachment.

BRIEF SUMMARY OF THE INVENTION

This invention relates to a faecal management device (10) comprising a bag (11) and a flange (12). The flange (12) comprises adhesive used to attach the device to the perianal area of the wearer. The invention resides principally in the provision of at least two non-adhesive lobes, i.e. one or more placement lobes (13) or one or more detachment lobes (14) or a combination thereof, on the flange (12). Said lobes (13) (14) can be used by a caretaker to handle the device with e.g. thumb and forefinger. Said lobes (13)/(14) are also useful for the detachment of the device and as a help in the peeling off of the release paper.

DETAILED DESCRIPTION OF THE INVENTION

Figure 1:
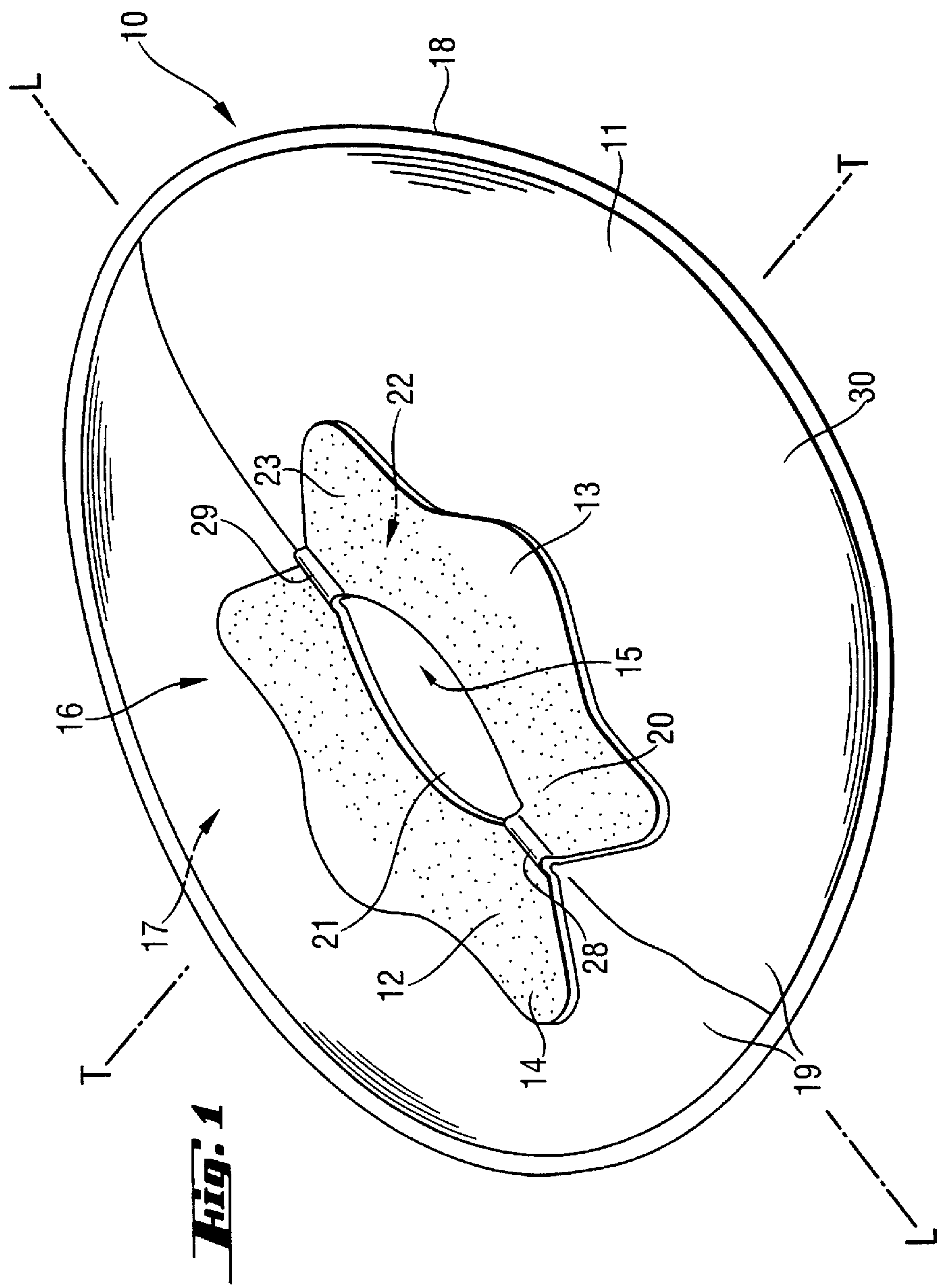
FIG. 1 is a perspective view of a preferred embodiment of the faecal management device. L denotes a longitudinal axis, T denotes a transversal axis.

The invention relates to a faecal management device (10) as shown in FIG. 1. The device (10) comprises a bag (11) and a flange (12).

Description of the Faecal Management Device as a Whole

Typically faecal management devices comprise a bag (11) having an aperture (21) and a flange (12) surrounding the aperture for preferably adhesive attachment to the perianal area of a wearer as visible from FIG. 1. Any faecal management device known in the art can be provided according to the present invention.

The bag (11) as used herein is a flexible receptacle for the containment of excreted faecal matter. The bag (11) can be provided in any shape or size depending on the intended use thereof, i.e. whether the device is intended for bedridden patients or active patients suffering from incontinence or requiring an artificial bowel or for infants. For example, elongated bags which are principally tubular or rectangular are typically utilized by bedridden patients and elderly incontinence sufferers. For more active wearers whether infants or adults, the faecal management device should preferably be anatomically shaped such that the device follows the contours of the body and can be worn inconspicuously by the wearer under normal garments.

Particularly, preferred shapes are flat circular type bags, cone shaped bags, truncated cone shaped bags and pyramidal or truncated pyramidal bags. In a most preferred embodiment of the present invention, the bag (11) has a substantially truncated cone shape. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag in-between the buttocks of the wearer and thereby ensure good contact between the flange and the skin of the wearer. For example, the bag (11) may be provided with a neck portion or conduit.

The bag (11) is preferably designed to provide sufficient volume for faecal material under a variety of wearing conditions, also when worn by a freely moving, i.e. not bedridden wearer. Sitting on the bag, for example, will result in a largely reduced volume in some areas of the bag. Thus, the bag is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapor such as water vapor in order to avoid the problem of entrapment and condensation of moisture vapor given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner surface (15) of the bag (11). Any known techniques for securing absorbent material to nonwoven and film substrates may be used to secure the absorbent material to the inner surface (15) of the bag. The absorbent material may also be arranged to have any desired shape or configuration (e.g., rectangular, oval, circular, etc.).

As shown in FIG. 1 the bag (11) is provided with an aperture (21) whereby faecal matter is received from the body prior to storage within the bag cavity. The aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction or in both directions, e.g. the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering faecal matter.

The flange may be provided in any size depending on the wearer group for which the device is intended. Similarly the flange may be provided in any shape and preferably has a symmetrical shape preferably comprising a plurality of lobes (13)/(14). The flange comprises a garment facing portion (22) and a wearer facing portion (23). In an preferred embodiment these are two large, substantially flat surfaces, however, the flange (12) may also comprise projections, a front projection (28) and/or a rear projection (29), designed to fit the perineal and/or coccygeal area of the wearer.

The flange (12) should be made of soft, flexible and malleable material to allow easy placement of the flange (12) to the perianal area. Typical materials include non-woven materials, wovens, open celled thermoplastic foams, closed-cell thermoplastic foams, composites of open celled foams and stretch non-woven, and films. A closed-cell foam of polyethylene has been found effective, but more preferably an open celled polyurethane foam is used. Preferably, such foams have a thickness within the general range of 0.1 to 5 millimeters and a density of 5 to 250 g/m$^2$, more preferably 50 g/m$^2$. Other thermoplastic foam materials, or other suitable plastics sheet materials having the described properties of such foams (i.e., softness, pliability, stretchability, and contractability) might also be used. Preferably, the material of garment facing portion (22) of the flange (12) may extend into the defined aperture area so as to form a skirt or flap of material which prevents unintentional adhesion of the surface edges of the flange (12) defining the aperture (21) to one another during use.

According to the present invention the faecal management device (10) further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconized paper. The adhesive (20) can cover the entire wearer facing portion (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing portion (23) of the flange (12), so as to provide lobes (13)/(14) on either side of the flange (12) which are non-adhesive and can thereby serve to facilitate placement and removal of the device while avoiding contact with the adhesive. These lobes (13)/(14) are however preferably also covered by the release means. Before application of the faecal management device (10) to the skin of the wearer, the release means if present is removed.

According to the present invention any medically approved water resistant pressure sensitive adhesive may be used to attach the device to the perianal area of the wearer, such as hydrocolloid adhesives and hydrogel adhesives. Particularly effective adhesives in providing the desired adhesive properties to secure the flange to the skin of the wearer at the sensitive perianal area, whilst allowing for relatively painless application and removal, are formed from crosslinking polymers with a plastisizer to form a 3-dimensional matrix.

The adhesive (20) can be applied to the wearer facing portion (23) of the flange (12) by any means known in the art such as slot coating, spiral, or bead application or printing. Typically the adhesive (20) is applied at a basis weight of from 20 $g/m^2$ to 2500 $g/m^2$, more preferably from 500 $g/m^2$ to 2000 $g/m^2$ most preferably from 700 $g/m^2$ to 1500 $g/m^2$ depending on the end use envisioned. For example, for faecal management devices (10) to be used for babies the amount of adhesive (20) may be less than for faecal management devices (10) designed for active adult incontinence sufferers.

Figure 2:
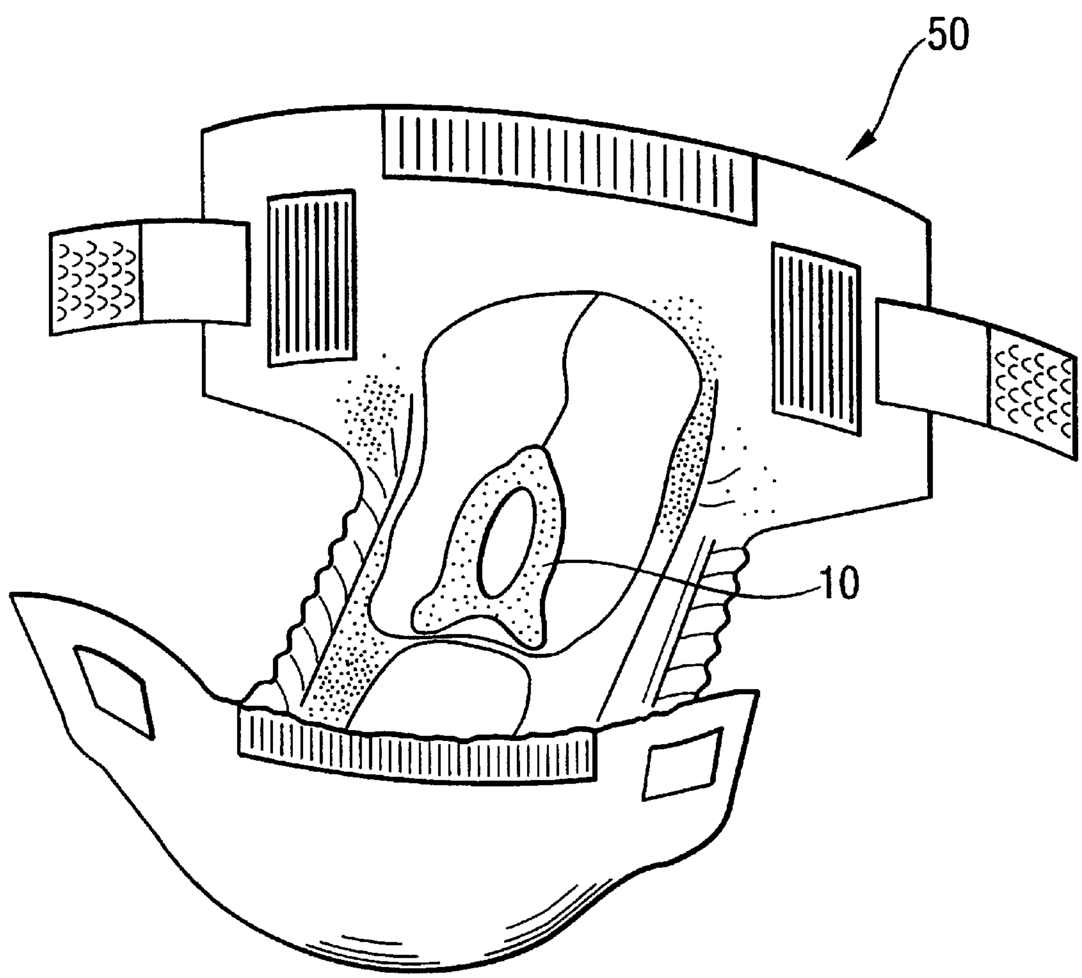
FIG. 2 is a perspective view of a diaper and a faecal management device, which can be worn in combination according to the present invention.

Detailed Description of a Diaper to be Worn in Combination with the Faecal Management Device The faecal management device (10) of the present invention has been found to be particularly useful and beneficial when used in conjunction with a garment, or diaper (50), preferably a disposable diaper—refer to FIG. 2. The faecal management device (10) is preferably first placed in the perianal area of the wearer before the disposable diaper (50) is applied. In particular, the diaper (50) is positioned over the faecal management device (10) and fastened in a conventional manner around the body of the wearer. It has been found that, in addition, to providing excellent separation between urine and faecal material, the combined faecal management device (10) and diaper (50) system actually reduces skin irritation, which may at times occur, especially since the group of typical wearers includes the very old, the very young and the unhealthy wearers. In effect, the presence of the faecal management device (10) permits the formation of a separation layer between the skin of the wearer and the diaper (50), i.e. a part of the absorbent core (58) of the diaper (10). The diaper (50) can be of the conventional type (an embodiment of which is described below although not a limiting example by any means) or can be adapted to contain in an effective and comfortable manner the faecal management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
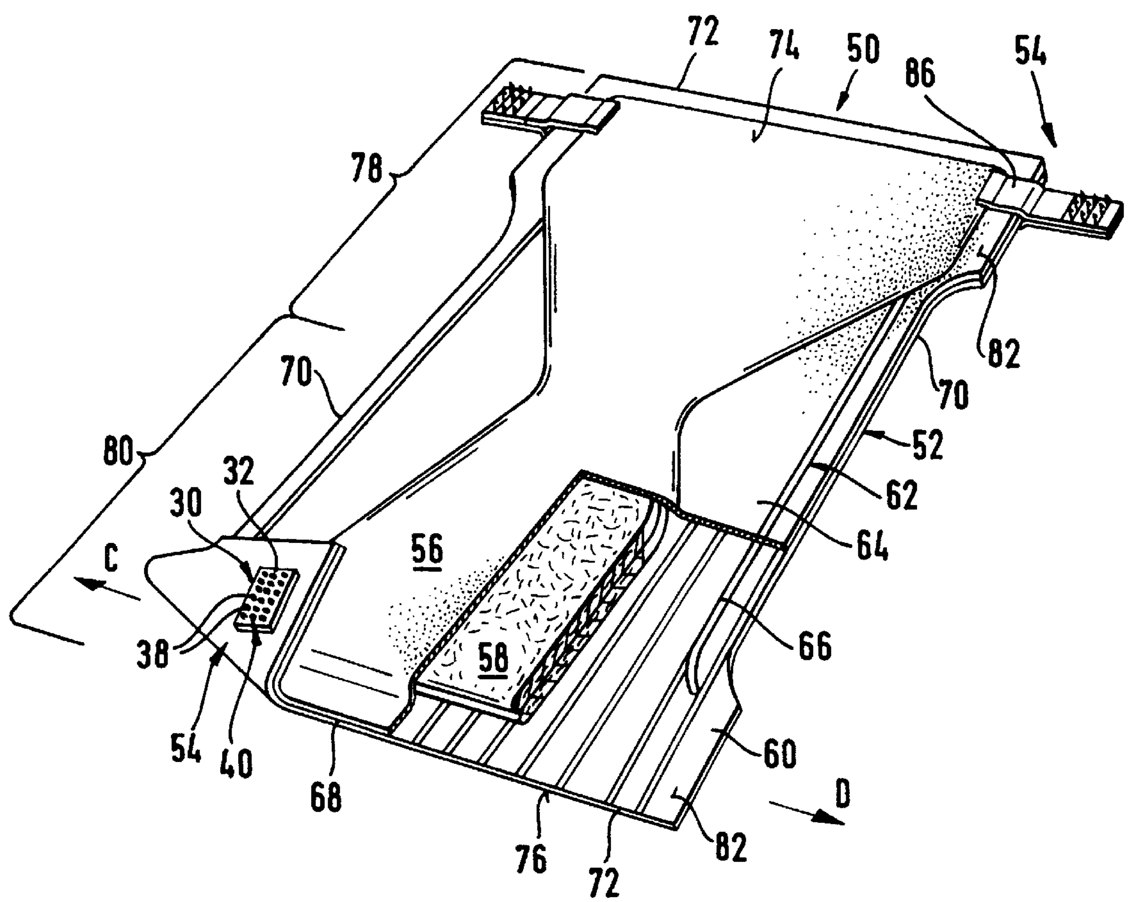
FIG. 3 is a partially cut-away perspective view of a diaper to be worn in combination with a faecal management device according to the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibers. Preferably, it is made of a material that isolates the skin of the wearer from liquids retained in the absorbent core (58).

There are a number of manufacturing techniques which may be used to manufacture the topsheet (56). For example, the topsheet (56) may be a non-woven web of fibers. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Detailed Description of the Lobes

The invention resides principally in the provision of at least two non-adhesive lobes, i.e. one or more placement lobes (13) or one or more detachment lobes (14) or a combination thereof, on the flange (12).

To allow a more detailed and clear description of the device, in the following paragraphs firstly a number of terms, as used herein, will be defined.

Regarding in particular the flange (12) the longitudinal axis is to be understood as follows: The direction which is substantially defined by the anal groove in the intended wearing position shall define the longitudinal direction. The longitudinal axis is an axis in the longitudinal direction, which crosses the center of the aperture (21). The most preferred indication of the intended wearing position is the presence of one or two projections (28) and/or (29) designed to fit the perineal or coccygeal area of the wearer, a less preferred indication of the intended wearing position is a fold in said flange (12) prior to use intended to be placed in parallel to the anal groove when placing the product. The longitudinal axis is typically also an axis of symmetry.

The transversal axis is an axis in the direction perpendicular to said longitudinal direction, which crosses said centre of said aperture (21).

The transversal axis is an axis in the direction perpendicular to said longitudinal direction, which crosses said center of said aperture (21).

The term contour is used with regard to flat objects, such as the flange (12), to denote the outer boundaries of the object as seen when looking perpendicularly onto the plane in which the object is flat.

The term center is used to describe a point of an object or a part of an object, which coincides with the centre of mass, if said object or part were of uniform density.

Centered on the longitudinal or the transversal axis is used if the center of an object lies on said longitudinal or transversal axis when looking onto the object from a direction which is perpendicular to both the longitudinal and the transversal axis.

A reference to the "lobes (13)/(14)" is to be understood as referring to both kinds of lobes, the placement lobes (13) and the detachment lobes (14).

The lobes (13)/(14) may comprise an integral or contiguous extension of the flange (12), or alternatively, may be made of a separate and independent piece of material joined to the flange (12). The lobes (13)/(14) have a wearer facing portion and a garment facing portion. The wearer facing portions of said placement lobes (13)/(14) are non-adhesive.

The term non-adhesive, as used herein, describes a low level of adhesion as compared to the parts of the flange (12) which are meant to adhere to the perianal area of the wearer. Preferably the adhesive forces on the non-adhesive parts are no more than 20% than the adhesive forces for attachment to the perianal area of the wearer, more preferably no more than 10% as measured by the adhesive forces test method described below. In any case the adhesive forces measured on the non-adhesive parts of the device (10) are no more than 0.5 N (50 g), preferably no more than 0.3 N (30 g) as measured by the adhesive forces test method described below. Thus, the non-adhesive lobes (13)/(14) are easier to detach from the skin in the anal region and from the skin of the fingers. Such a low level of adhesion can be achieved in various ways: Preferably the non-adhesive areas are completely or largely free of adhesive. The low level of adhesion can also be achieved by covering an adhesive present on said surface to reduce adhesion, e.g. by talcum or by a solid non-adhesive layer of any kind, such as paper. If said non-adhesive layer covering said adhesive is used, said non-adhesive layer is not intended to be removed at any time by the caretaker or wearer, thus not being readily removable or releasable.

Figure 4:
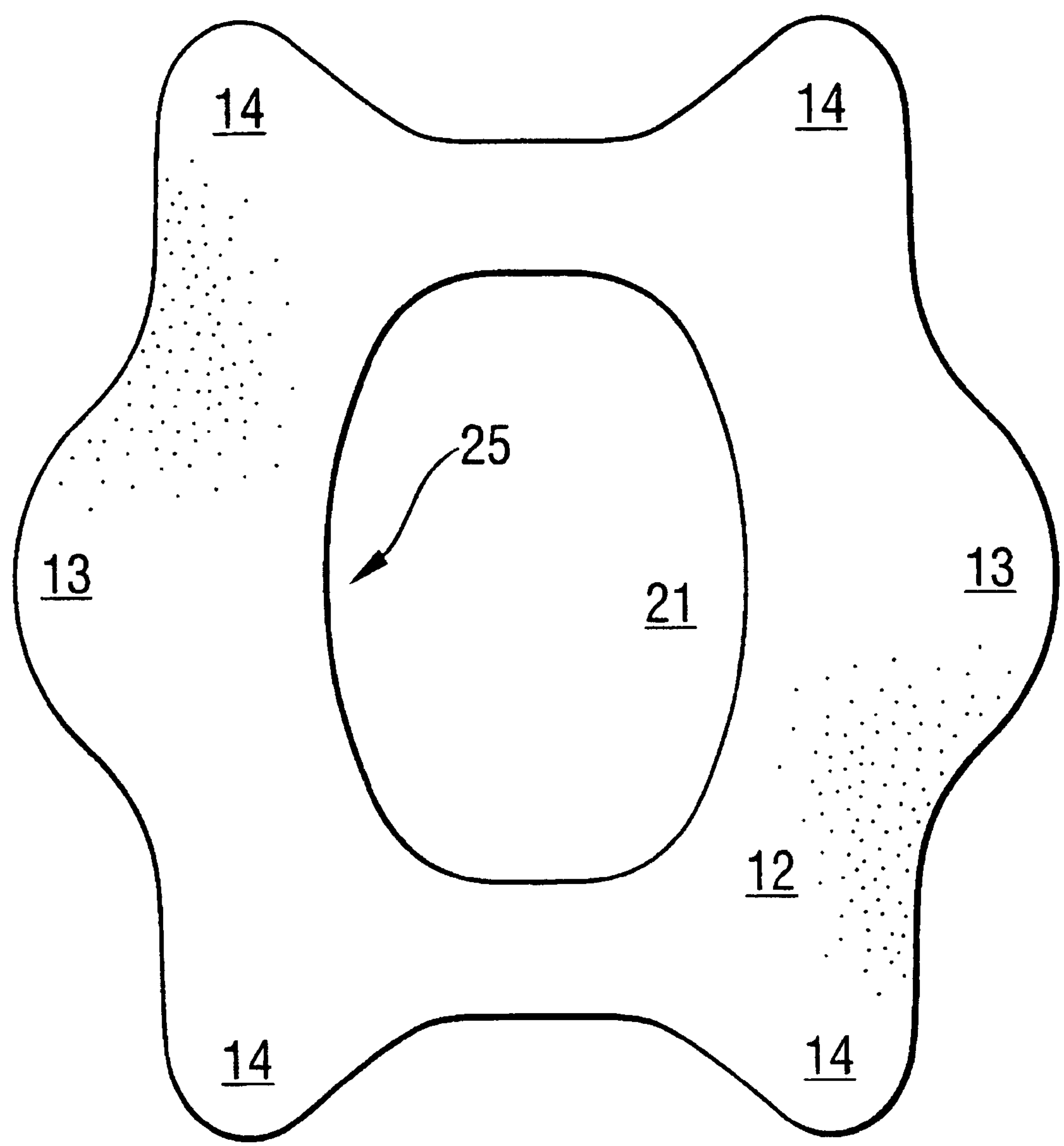
FIG. 4 is a top plain view onto the flange comprising placement lobes and detachment lobes.

The lobes (13)/(14) extend outward from the contour of the flange (12); typically in such a direction that the wearer facing portion of the lobes (13)/(14) is in the same plane as the adjacent areas of the wearer facing portion (23) of the flange (12). In a preferred embodiment the lobes (13)/(14) are generally a convex extension of the contour of the flange (12) without lobes (13)/(14), as seen in FIG. 4. The shape of each lobe (13) or (14) can be independently chosen, preferably all placement lobes (13) are of an identical first shape and all detachment lobes (14) are of an identical second shape. Most preferably, the detachment lobes (14) are of a more curved convex contour than the detachment lobes (13), as depicted in FIG. 4.

The size of the lobes (13)/(14) is such, that they can be gripped easily with the fingers, typically thumb and forefinger of an adult caretaker.

For the placement lobes (13) the surface area on the wearer facing portion is independently preferably from 0.5 $cm^2$ to 20 $cm^2$, more preferably from 1 $cm^2$ to 10 $cm^2$, even more preferably from 3 $cm^2$ to 7 $cm^2$. Preferably all placement lobes (13) have a substantially identical surface area.

For the detachment lobes (14) the surface area on the wearer facing portion may be chosen as for the placement lobes (13). Most preferably said surface area of the detachment lobes (14) is chosen from 10 to 30% smaller than for the placement lobes (13), yet still large enough for easy gripping. Preferably all detachment lobes (14) have a substantially identical surface area.

The flange (12) is preferably provided with at least two placement lobes (13). In a preferred embodiment the same number of placement lobes (13) are located on each side of the flange (12). In an even more preferred embodiment the flange (12) including the placement lobes (13) is symmetrical about the longitudinal axis. In an even more preferred embodiment the centers of the placement lobes (13) on either side of the flange (12) have the same distance to the transversal axis. In the most preferred embodiment two placement lobes (13) are centered on the transversal axis. The provision of two placement lobes (13) and in particular their preferred positioning as described above make it particularly easy for the person handling the device to hold the device with one hand, e.g. thumb and forefinger, using the placement lobes and to remove a release means, which may cover the adhesive (20), using the other hand.

Said placement lobes (13) can comprise any material, preferably any material comprised by the flange (12) for which typical materials are listed above. In order to improve the physical or other properties of the placement lobes (13), they may comprise additional material or additives or a different material composition not comprised by the flange (12), or additional layers of a material also comprised by the flange (12).

The placement lobes (13) preferably exhibit a degree of stiffness which allows to transmit forces in the direction of the flange (12). The stiffness measured for the lobes by the flexibility test method described below is preferably in the range of 0.005 to 0.2 N (0.5 to 20 g).

According to the present invention the placement lobes (13) can also be used for the detachment of the faecal management device (10) from the wearer. Since the placement lobes (13) are non-adhesive, they are easier to grip than the flange (12) itself and furthermore avoid all the previously mentioned disadvantages associated with gripping the flange (12). The provision of at least two non-adhesive lobes, i.e. one or more placement lobes (13) or one or more detachment lobes (14) or a combination thereof, furthermore allows the detachment of the faecal management device (10) from both sides. This is particularly desirably as a detachment from one side may be impossible due the position of the wearer, in particular in the case of a bedridden patient. Furthermore the detachment of the device by gripping only one lobe, may be impossible or lead to damage (and thus leaking) of the device, especially if a soft and small flange (12) is used (as to better conform to the body of the wearer), which is easily tearable, such as a non-woven.

As a detachment aide in addition to the placement lobes (13) or in absence thereof, the flange (12) may comprise detachment lobes (14). Preferably two or four detachment lobes (14) are used, most preferably four.

A different positioning of the detachment lobes (14) to the positioning of the placement lobes (13) is normally beneficial for easier detachment in placing the product, the buttocks of the wearer may have to be spread apart. Such an extra effort is not necessary for detachment, if detachment lobes (14) are provided so positioned that they are not covered much by the buttocks of the wearer. Consequently the detachment of the device can be made considerably more convenient for both, the caretaker and the wearer.

In a preferred embodiment the detachment lobes (14) are positioned symmetrical about said longitudinal axis. More preferably they are positioned nearer to said longitudinal axis than to said transversal axis, as depicted in FIG. 4. The provision of four detachment lobes (14) as shown in FIG. 4 allows detachment of the device largely independent of the position of the wearer.

The material of the detachment lobes (14) may be chosen as for the placement lobes (13). However, they can be made less stiff than the placement lobes (13). Furthermore, they preferably are to be made to withstand the tearing forces typically to be expected in the detachment process, which depends inter alia on the adhesive used for attachment. The detachment lobes (14) may therefore comprise additional material or additives or a different material composition as compared to the flange (12) and the placement lobes (13) to increase their strength with regard to tearing.

The adhesive (20) on the wearer facing portion (23) of the flange (12) is preferably covered with a release means (not shown) in order to protect the adhesive (20), such as siliconized paper. The lobes (13)/(14) are preferably also covered by the release paper. In another preferred embodiment only some of said lobes are covered with a release means. Before application of the faecal management device (10) to the skin of the wearer, the release means if present is removed. Since the lobes are non-adhesive, gripping of those portions of the release means, which cover said lobes (13)/(14), is particularly easy, also due to the provision of a plurality of lobes (13)/(14).

A faecal management device (10) according to the present invention will typically be placed onto the perianal area of a wearer by the following handling steps: Removing the release means (if present) covering the adhesive (20) of the device (10); grasping said placement lobes (13) with one or both hands, typically with thumb and forefinger of one hand; placing said device (10) in the perianal area of the wearer while holding said device (13) by said placement lobes (13); letting said adhesive (20) on said flange (12), attach to the body of the wearer, preferably by exercising some pressure towards the wearer, more preferably by exercising some pressure towards the anal opening of the wearer, most preferably by exercising some pressure towards the anal opening of the wearer and towards the buttocks of the wearer; releasing the grasp of both of said placement lobes (13).

The detachment of a faecal management device (10) according to the present invention will typically comprise the following steps: grasping with one or both hands, typically using thumb and forefinger of each hand, one or more of said lobes on said flange (12), i.e. one or more of said placement lobes (13) or one or more of said detachment lobes (14) or a combination thereof, preferably one or more of said detachment lobes (14); exercising forces directed substantially away from the wearer; holding the detached device (10) using said lobes on said flange (12); releasing the grasp of said lobes used for holding the detached device (10).

Depending on the used embodiment of the present invention and conditions of the placement, usage and detachment of the device (10) numerous other handling steps in placing and detaching the device (10) may also be undertaken, different handling steps may be undertaken or certain of the mentions handling steps may not be involved.

Adhesive Forces Test Method

Intent

The purpose of this method is to determine the adhesive forces due to a contact with an adhesive surface S. The method is based on the pull force required to remove a piece of cotton from the adhesive surface S.

Test Conditions

Standard conditions are temperature of 23°±2° C. and a relative humidity at that temperature of 50±2%. All tests shall be conducted in the conditioned chamber or room under standard conditions.

The test specimen of the adhesive surface S shall be 20±2 mm wide and 50 mm in length. (The test specimen may have to be provided from a material identical to the material used for said lobes, if the lobes are not large enough.)

Equipment

Tensile Tester

Instron Tester Model 6021 or equivalent—Test speed 1000 mm/min

Mechanical Weight

Mechanical weight driven by the tester to move 1000 mm/min in a direction and in the opposite after application of 1 Kg of mass for 30 sec on adhesive surface S.

Piece of Cotton

The piece of cotton shall be 20±2 mm wide and 50 mm in length

Sample Preparation and Execution

Clamp the weight into the upper jaw of the adhesion tester machine. Operate the upper jaw at 1000 mm/min in down direction (compression phase) allowing the mechanical weight to match exactly the adhesive surface S covered by the piece of cotton to rest on the stationary portion of adhesion testing apparatus during the weight application period (30 s). Return the upper jaw at the same speed in the opposite direction pulling the piece of cotton and the adhesive surface S apart and use the peak pull value obtained as the pull stickiness adhesion value.

Report

Report the average of 2 pull peaks in N.

Flexibility Test Method

The following test method is utilized to determine the flexibility or stiffness of samples of the lobes when the sample is compressed in the machine direction.

In principle the test method measures the average force required to compress/fold the sample in machine direction at a force range of 0.02 to 0.3 Newtons.

Equipment

Tensile Tester: Instron (Mod: 6021); scissors

Tensile Tester Setting

1. Calibrate the Load Cell (10 Newton).
2. Set the Tensile Tester to run a Compression test.
3. Set clamp distance at 50 mm.
4. Set test speed at 100 mm/minute.
5. Set the dimension of the deformation at 35 mm.
6. Set the Tensile Tester to acquire Average Load (Newton).

Sample Preparation

1. Test samples are prepared by cutting using scissors 3 samples of 6×2 cm.
2. If present release paper is removed from the samples.

Test Operation

1. Tensile tester setting
2. Place the samples between the clamps, placing them symmetrically to the clamps.
3. Run the test on a minimum of 3 samples.

Report

The average force of 3 tests in N (Newton).

What is claimed is:

1. Faecal management device comprising a bag said bag having an aperture and a generally planar flange surrounding said aperture, said flange having a wearer facing portion and a garment facing portion wherein said wearer facing portion comprises a layer of adhesive for releasable attachment to the perianal area of a wearer, said flange further comprising a longitudinal axis and a transversal axis orthogonal thereto, said flange further comprising at least two non-adhesive lobes on each side of said longitudinal axis, wherein said lobes extend radially outwardly from said aperture, said flange further comprising at least one elongate projection extending outwardly from said plane of said flange, said projection being coincident said longitudinal axis.

2. Faecal management device (10) according to claim 1, said flange (12) having a longitudinal axis of symmetry, wherein said placement lobes (13) and said detachment lobes (14) are symmetrical about said longitudinal axis.

3. Faecal management device (10) according to claim 1, comprising two placement lobes (13).

4. Faecal management device according to claim 1, comprising at least two detachment lobes on each side of said transverse axis.

5. Faecal management device (10) according to claim 3, said device having a longitudinal and a transversal axis, wherein said two placement lobes (13) are centred at said transversal axis.

6. Faecal management device according to claim 6, wherein each of said lobes is free of said adhesive.

7. Faecal management device (10) according to claim 1, wherein a release means covers said adhesive (20) and said lobes (13)/(14).

* * * * *